(12) United States Patent
Schuurkes et al.

(10) Patent No.: US 8,063,069 B2
(45) Date of Patent: Nov. 22, 2011

(54) PRUCALOPRIDE-N-OXIDE

(75) Inventors: Joannes Adrianus Jacobus Schuurkes, Beerse (BE); Willy Joannes Carolus Van Laerhoven, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 1057 days.

(21) Appl. No.: 11/928,528

(22) Filed: Oct. 30, 2007

(65) Prior Publication Data

US 2008/0125464 A1    May 29, 2008

Related U.S. Application Data

(63) Continuation of application No. 10/501,346, filed as application No. PCT/EP03/00276 on Jan. 13, 2003, now abandoned.

(30) Foreign Application Priority Data

Jan. 16, 2002 (EP) ..................................... 02075157

(51) Int. Cl.
*A61K 31/445* (2006.01)
*C07D 405/12* (2006.01)
(52) U.S. Cl. ....................................... 514/320; 546/196
(58) Field of Classification Search .................. 514/320; 546/196
See application file for complete search history.

(56) References Cited

U.S. PATENT DOCUMENTS 5,374,637 A    12/1994    Van Daele et al.

FOREIGN PATENT DOCUMENTS

| EP | 0 299 586 B1 | 4/1994 |
|---|---|---|
| EP | 0 389 037 B1 | 9/1995 |
| EP | 0 445 862 B1 | 4/2000 |
| WO | WO 96/10027 A1 | 4/1996 |
| WO | WO 96/16060 A1 | 5/1996 |
| WO | WO 97/24356 A1 | 7/1997 |
| WO | WO 97/30031 A1 | 8/1997 |
| WO | WO 97/31897 A1 | 9/1997 |
| WO | WO 00/30640 A1 | 6/2000 |
| WO | WO 00/66170 A1 | 11/2000 |

OTHER PUBLICATIONS

Seddon "Pseudopolymorph . . ." Crustal Growth & designe 4(6) 1087 (2004) (two pages from internet.*
Braga et a;/ "Making crystals form crystals . . . " Royal Soc. Chem. Chem. Commun. p. 3635-3645 (2005).*
PCT Search Report for PCT/EP03/00276 mailed Mar. 31, 2003.
International Preliminary Examination Report for PCT/EP03/00276, 2003.

* cited by examiner

*Primary Examiner* — Celia Chang

(57) ABSTRACT

The present invention is concerned with a novel benzamide derivative and the pharmaceutically acceptable acid addition salts thereof, pharmaceutical compositions comprising said novel compound, processes for preparing said compounds and compositions, and the use thereof as a medicine in the treatment of gastrointestinal motility disorders.

7 Claims, No Drawings

PRUCALOPRIDE-N-OXIDE

CROSS REFERENCE TO RELATED APPLICATIONS

This application is a continuation of U.S. Ser. No. 10/501,346, filed Jul. 13, 2004, now abandoned the disclosure of which is hereby incorporated by reference, which is a national stage of Application No. PCT/EP03/00276, filed Jan. 13, 2003, which application claims priority from EPO Application No. 02075157.4, filed Jan. 16, 2002.

The present invention is concerned with a novel benzamide derivative and the pharmaceutically acceptable acid addition salts thereof, pharmaceutical compositions comprising said novel compound, processes for preparing said compounds and compositions, and the use thereof as a medicine in the treatment of gastrointestinal motility disorders.

EP-0,445,862-A, published on Sep. 11, 1991, N-(4-piperidinyl) (dihydrobenzo-furan or dihydro-2H-benzopyran)carboxamide derivatives are disclosed having gastrointestinal motility stimulating properties.

WO-96/16060, published on 30 May 1996, specifically discloses the compound 4-amino-5-chloro-2,3-dihydro-N-[1-(3-methoxypropyl)-4-piperidinyl]-7-benzofuran-carboxamide which is generically known as "prucalopride".

The compounds of the present invention differ therefrom by the fact that they invariably contain a 1-piperidine oxide moiety and by their improved pharmacological properties.

The present invention concerns a compound of formula (I)

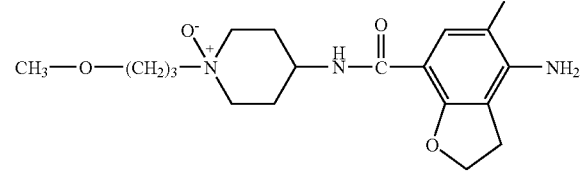

(I)

and stereochemically isomeric forms and pharmaceutically acceptable acid addition salts thereof.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, the substituents on the piperidine moiety have either the cis- or trans-configuration.

Stereochemically isomeric forms of the compounds of formula (I) are obviously intended to be embraced within the scope of this invention.

The pharmaceutically acceptable acid addition salts as mentioned hereinabove are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term addition salt as used hereinabove also comprises the solvates which the compounds of formula (I) as well as the salts thereof, are able to form. Such solvates are for example hydrates, alcoholates and the like.

The compounds of formula (I) can be prepared following art-known procedures for converting a trivalent nitrogen into its N-oxide form. Said N-oxidation reaction may generally be carried out by reacting a compound of formula (II) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

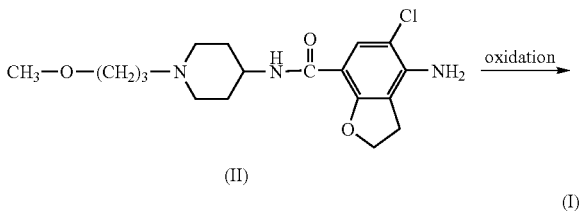

(II)

(I)

The compounds of formula (I) as prepared in the hereinabove described process may be synthesized in the form of mixture of cis- and trans-stereoisomers which can be separated from one another following art-known resolution procedures. Alternatively, depending upon the reaction conditions of the oxidation reaction, said oxidation reaction may yield either the cis-stereoisomer or the trans-stereoisomer.

The compounds of formula (II) are known compounds and can be prepared according to the procedures described in WO-96/16060.

Upon oral administration the N-oxide compounds of formula (I) of the present invention are converted into compounds of formula (II) by bacterial or enzymatic reduction. Furthermore it was found that unexpectedly systemic exposure to compounds of formula (II) was lower upon oral administration of a N-oxide compound of formula (I) compared to oral administration of an equimolar amount of compound of formula (II) while the motility enhancing effect remains. A lower systemic exposure may be beneficial in reducing potential adverse effects.

The compound of formula (II), generically known as prucalopride, facilitates both cholinergic and non-cholinergic non-adrenergic (NANC) excitatory neurotransmission and stimulates colonic motility and defecation in animals. It has no affinity for $5-HT_{2A}$ and $5-HT_{3A}$ receptors but is a potent and selective agonist of $5-HT_4$ receptors. Prucalopride induces giant contractions in the colon that are propagated over the length of the colon as a peristaltic wave and therefore has significant motility enhancing effects on the large intestine. Furthermore, it is believed that prucalopride is also useful for the treatment of upper GI tract motility disorders such as gastro-oesophageal reflux.

In view of its enterokinetic properties, prucalopride is useful in the treatment of motility disorders of the intestinal system, such as, e.g. gastroparesis, dyspepsia, constipation, pseudo-obstruction, intestinal atony, post-operative intestinal atony, irritable bowel syndrome (IBS), and drug-induced delayed transit. The subject compounds may also be used to facilitate large bowel cleaning or to facilitate intubation and/or endoscopy. Said method comprises the systemic administration of an effective motility stimulating amount of prucalopride to warm-blooded animals, including humans.

In view of the utility of the compounds of formula (I), it follows that the present invention also provides a method of treating warm-blooded animals, including humans, (generally called herein patients) suffering from motility disorders of the intestinal system. Consequently a method of treatment is provided for relieving patients suffering from conditions, such as, for example, constipation, pseudo-obstruction, intestinal atony, post-operative intestinal atony, irritable bowel syndrome (IBS), drug-induced delayed transit, large bowel cleaning.

Hence, the use of a compound of formula (I) as medicine is provided, and in particular the use of a compound of formula (I) for the manufacture of a medicine for treating conditions involving a disordered motility or transit of the upper and lower gastrointestinal tract.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

The formulations of the present invention may optionally include an anti-flatulent, such as simethicone, alpha-D-galactosidase and the like. Furthermore, the formulations may optionally comprise other active ingredients e.g. δ-opiate antagonists such as naltrindole and the like.

In general it is contemplated that a therapeutically effective amount would be from about 0.001 mg/kg to about 2 mg/kg body weight, preferably from about 0.02 mg/kg to about 0.5 mg/kg body weight. A method of treatment may also include administering the active ingredient on a regimen of between two or four intakes per day, or on demand.

The amount of prucalopride-N-oxide, or a pharmaceutically acceptable acid addition salt thereof, required as daily dose in treatment will vary not only with the route of administration, the nature of the condition being treated and the age, weight and condition of the patient and will ultimately be at the discretion of the attendant physician. In general, however, a suitable daily dose will be in the range of from about 0.05 to about 200 mg per day, in particular from about 0.1 to 20 mg per day, more particular from about 0.5 to 10 mg per day. A suitable daily dose for use in prophylaxis will generally be in the same range. It may be appropriate to administer the required dose as two, three, four or more sub-doses at appropriate intervals throughout the day. Administration can be before or after the intake of food (i.e. preprandial or postprandial).

EXPERIMENTAL PART

A. Preparation

For some chemicals the chemical formula was used, e.g. $CH_3CN$ for acetonitril, $CH_2Cl_2$ for dichloromethane, $NH_4OAc$ for ammonium acetate and $CH_3OH$ for methanol.

Example A.1

4-Amino-5-chloro-2,3-dihydro-N-[1-(3-methoxypropyl)-4-piperidinyl]-7-benzofuran-carboxamide (0.012 mol) was dissolved in dichloromethane (200 ml) and 3-chloro-benzenecarboperoxoic acid (0.015 mol) was added. This mixture was stirred for 3 hours at room temperature. The mixture was diluted with aqueous ammonia and the resulting precipitate was filtered off and recrystallized from $CH_3CN$/2-propanol. The precipitate was filtered off and dried, yielding 2.15 g of cis-4-amino-5-chloro-2,3-dihydro-N-[1-(3-methoxypropyl)-4-piperidinyl]-7-benzofurancarboxamide, N-oxide monohydrate (compound (1), mp. 179.8° C.).

Example A.2

4-Amino-5-chloro-2,3-dihydro-N-[1-(3-methoxypropyl)-4-piperidinyl]-7-benzofuran-carboxamide (0.05 mol) was dissolved in dichloromethane (500 ml) and 3-phenyl-2-(phenylsulfonyl)-oxaziridine (Davis' reagent) (0.055 mol) was added. This mixture was stirred for 4 hours at room temperature. The mixture was concentrated to a volume of about 200 ml and the resulting precipitate was filtered off, dried and was purified by column chromatography over silica gel (eluent: $CH_2Cl_2$/$CH_3OH$ 95/5). The pure fractions were collected and the solvent was evaporated. The residue was triturated in DIPE, filtered off and dried and purified by high-performance liquid chromatography over RP-18 (eluent: (0.5% $NH_4OAc$ in $H_2O$)/$CH_3CN$ 85/15 v/v). The pure fractions were collected and the solvent was evaporated. The residue was triturated in DIPE, filtered off and dried, yielding 1.26 g trans-4-amino-5-chloro-2,3-dihydro-N-[1-(3-methoxypropyl)-4-piperidinyl]-7-benzofurancarboxamide, N-oxide monohydrate (compound (2), mp. 230° C.).

B. Pharmacological Examples

Example B.1

Two male beagle dogs were dosed orally with 1 ml of a test formulation comprising 2.5 mg/kg of 4-amino-5-chloro-2,3-dihydro-N-[1-(3-methoxypropyl)-4-piperidinyl]-7-benzofuran-carboxamide ("prucalopride").

After a wash-out period of four weeks, the same two dogs were dosed orally with 1 ml of a test formulation comprising 2.61 mg/kg of compound (1).

Blood samples were taken via the jugular vein immediately before dosing (blank sample) and at 0.25 h, 0.5 h, 1 h, 1.5 h, 2 h, 4 h, 6 h, 8 h, and 24 h after dosing. Aliquots of 10 ml were collected in EDTA tubes. Immediately after collection of the blood samples, plasma samples were prepared by centrifugation at approximately 1700×g for approximately 10 minutes.

Concentrations of prucalopride in the plasma samples were determined by LC/MS/MS. The quantification limit for prucalopride was 5.0 ng/ml.

Based on the individual plasma concentration-time data, using the actual sampling times, the following pharmacokinetic parameters were determined for prucalopride after oral administration of prucalopride and compound (1) and summarized in Table 1.

$C_{max}$ peak plasma concentration, determined by visual inspection of the data $T_{max}$ time to reach the peak plasma concentration, determined by visual inspection of the data.

$AUC_{0-\infty}$ area under the plasma concentration-time extrapolated to infinity

TABLE 1

| pharmacokinetic parameters for prucalopride after single oral administration of prucalopride and compound (1) | | | | |
|---|---|---|---|---|
| | oral administration of prucalopride | | oral administration of compound (1) | |
| | Dog 1 | Dog 2 | Dog 1 | Dog 2 |
| $C_{max}$ | 556 ng/ml | 660 ng/ml | 222 ng/ml | 488 ng/ml |
| $T_{max}$ | 1.0 h | 0.5 h | 2.0 h | 2.0 h |
| $AUC_{0-\infty}$ | 4226 ng·h/ml | 4372 ng·h/ml | 2265 ng·h/ml | 4093 ng·h/ml |

As can be seen in Table 1, oral administration of compound (1) gives a lower peak plasma concentration $C_{max}$ of prucalopride and the time $T_{max}$ to reach said $C_{max}$ is later. Hence systemic exposure to prucalopride after oral administration of compound (1) is substantially lower then after oral administration of prucalopride itself.

The invention claimed is:

1. A monohydrate compound of formula (I)

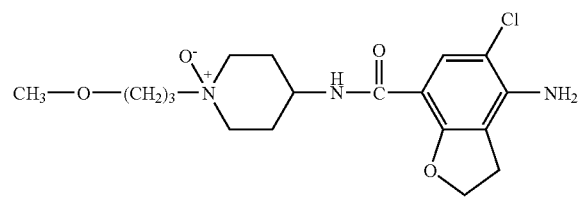

(I)

and stereochemically isomeric forms.

2. A compound as claimed in claim 1 having the cis configuration.

3. A compound as claimed in claim 1 having the trans configuration.

4. A pharmaceutical composition comprising a pharmaceutically acceptable carrier and a therapeutically active amount of a compound as claimed in claim 1.

5. A process for preparing a compound of formula (I) by oxidizing a compound of formula (II) with a suitable oxidants in a reaction-inert solvent.

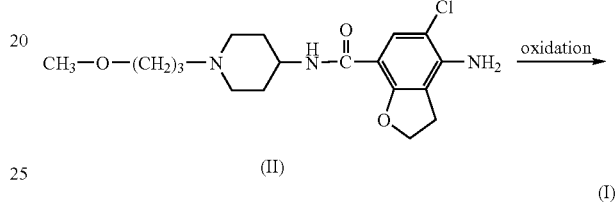

6. A method for treating a motility disorder of the intestinal system selected from the group consisting of gastroparesis, dyspepsia, constipation, pseudo-obstruction, intestinal atony, post-operative intestinal atony, irritable bowel syndrome (IBS) and drug-induced delayer transit comprising administering to a warm-blooded animal suffering from said motility disorder an effective amount of a compound as claimed in claim 1.

7. A method for facilitating a large bowel cleaning, intubation or endoscopy comprising administering to a warm-blooded animal in need of such large bowel cleaning, intubation or endoscopy an effective amount of a compound as claimed in claim 1.

* * * * *